(12) United States Patent
Paulsen (10) Patent No.: US 8,685,706 B2
(45) Date of Patent: Apr. 1, 2014

(54) ARID LAND SOIL CRUST RESTORATION

(75) Inventor: Steven R. Paulsen, Kimberly, ID (US)

(73) Assignee: Living Earth, LLC, Kimberly, ID (US)

(*) Notice: Subject to any disclaimer, the term of this patent is extended or adjusted under 35 U.S.C. 154(b) by 542 days.

(21) Appl. No.: 12/942,963

(22) Filed: Nov. 9, 2010

(65) Prior Publication Data

US 2011/0281331 A1 Nov. 17, 2011

Related U.S. Application Data

(60) Provisional application No. 61/259,517, filed on Nov. 9, 2009.

(51) Int. Cl.
*A01N 25/00* (2006.01)
*C05F 11/08* (2006.01)
*C12N 1/12* (2006.01)

(52) U.S. Cl.
USPC ............ 435/257.1; 71/6; 71/64.08; 71/64.1; 71/903; 435/946

(58) Field of Classification Search
None
See application file for complete search history.

(56) References Cited

U.S. PATENT DOCUMENTS

| 3,969,844 A | 7/1976 | Fogel et al. |
| 5,522,985 A | 6/1996 | Bender et al. |
| 2009/0056214 A1 | 3/2009 | Dody et al. |

FOREIGN PATENT DOCUMENTS

| DE | 102010019420.4 | 11/2011 |
| EP | 0246281 | 11/1987 |
| JP | 11107286 | 4/1999 |

OTHER PUBLICATIONS

Larry L. St. Clair, Jefferey R. Johansen and Bruce L. Webb, Rapid Stabilization of Fire-Disturbed Sites Using a Soil Crust Slurry: Inoculation Sudies, Reclamation and Revegetion Research, 1986, pp. 261-269, vol. 4, Elsevier Science Publishers B. V., Amsterdam, The Netherlands.

Jeffrey R. Johansen, Cryptogamic Crusts of Semiarid and Arid lands of North America, J. Phycol., 1993, pp. 140-147, vol. 29, Department of Bilogy, John Carroll University, Ohio, USA.

*Primary Examiner* — Debbie K Ware
(74) *Attorney, Agent, or Firm* — Thompson Coburn LLP; Charles P. Romano (57) ABSTRACT

The present invention relates to a process for restoring disturbed arid land soil crust. According to the process, site-sourced biological soil crusts (BSC) serve as sources for liquid suspension inoculants onto degraded arid lands. The BSC are gathered from near the disturbed site, and organisms from them are cultured, replicated and multiplied many times, preferably off-site. Then, this inoculant resulting from the indigenous population is distributed live and active in a liquid suspension over the entire area of the disturbed site.

12 Claims, 6 Drawing Sheets

Figure 2:
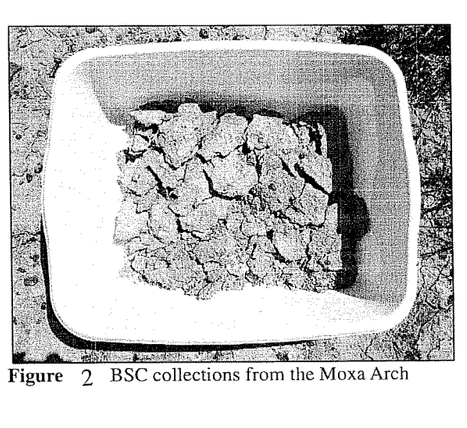

Figure 2 BSC collections from the Moxa Arch

Figure 1:
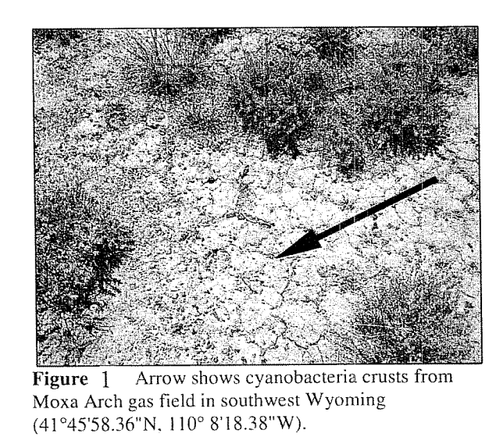

Figure 1 Arrow shows cyanobacteria crusts from Moxa Arch gas field in southwest Wyoming (41°45′58.36″N, 110° 8′18.38″W).

Figure 3:
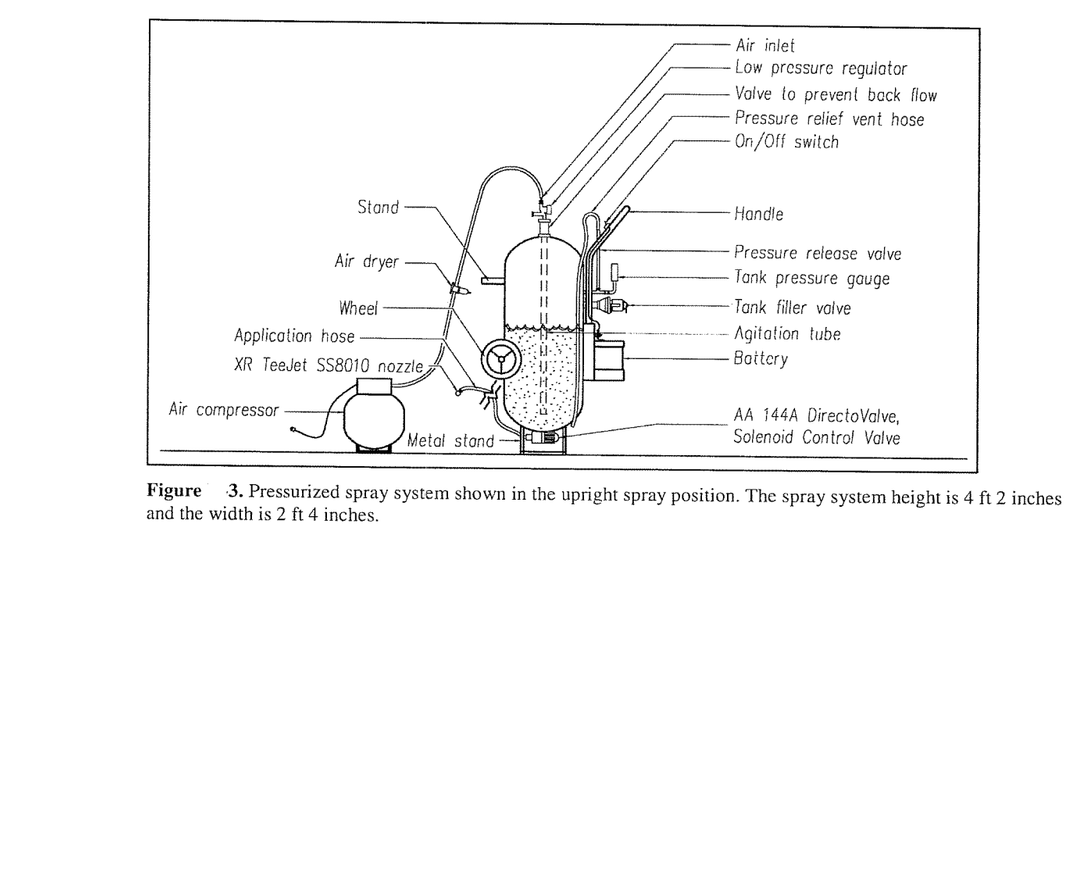

Figure 3. Pressurized spray system shown in the upright spray position. The spray system height is 4 ft 2 inches and the width is 2 ft 4 inches.

Figure 5:
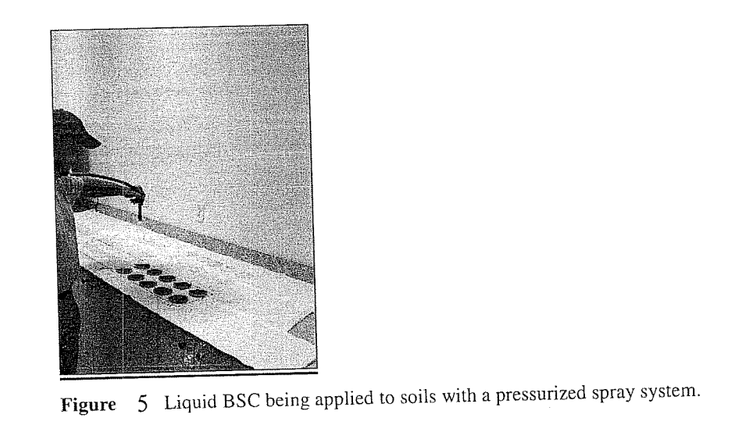

Figure 5. Liquid BSC being applied to soils with a pressurized spray system.

Figure 4. AA144A Dir

Figure 6:
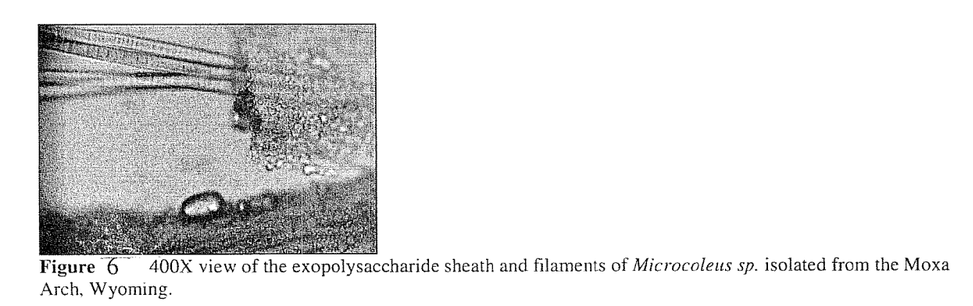

Figure 6 400X view of the exopolysaccharide sheath and filaments of *Microcoleus sp.* isolated from the Moxa Arch, Wyoming.

Figure 8:
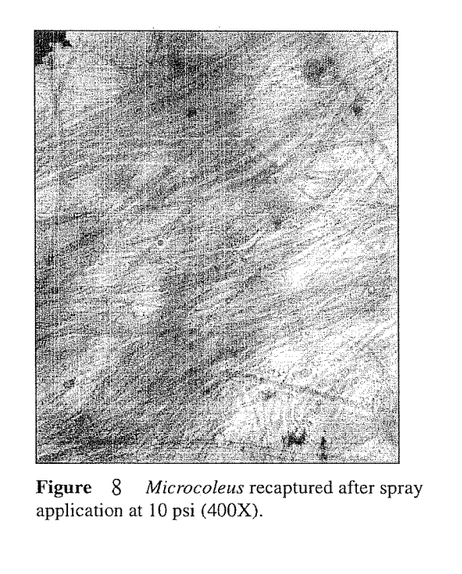
Figure 9A:
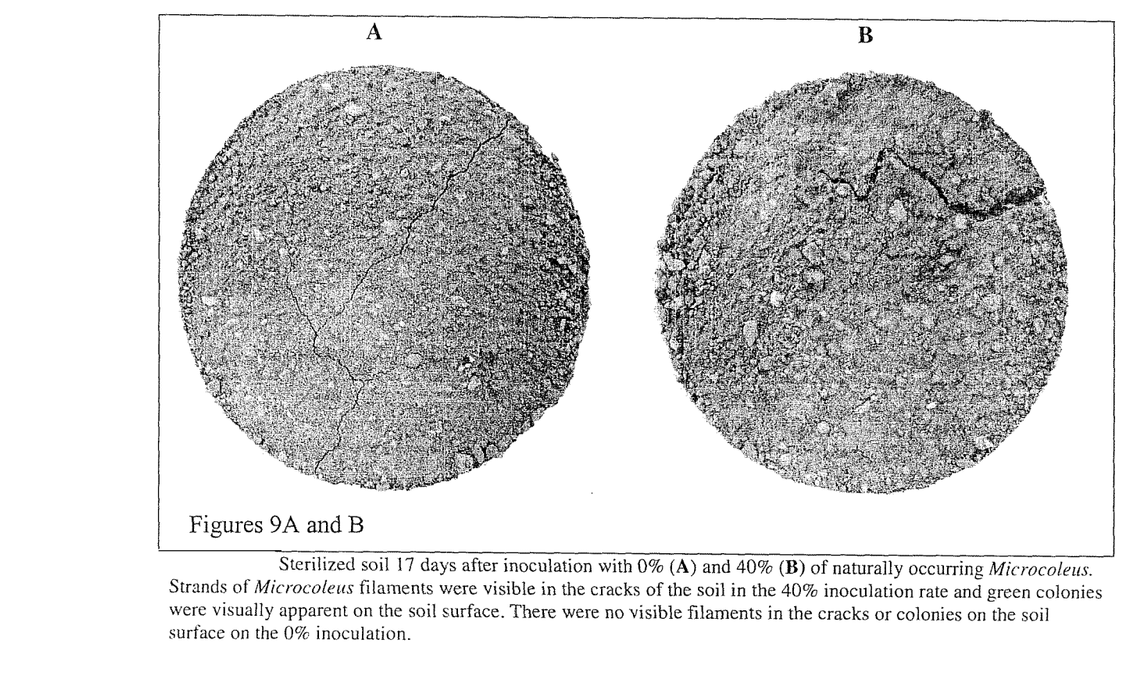

Figure 8 *Microcoleus* recaptured after spray application at 10 psi (400X).

Figure 7:
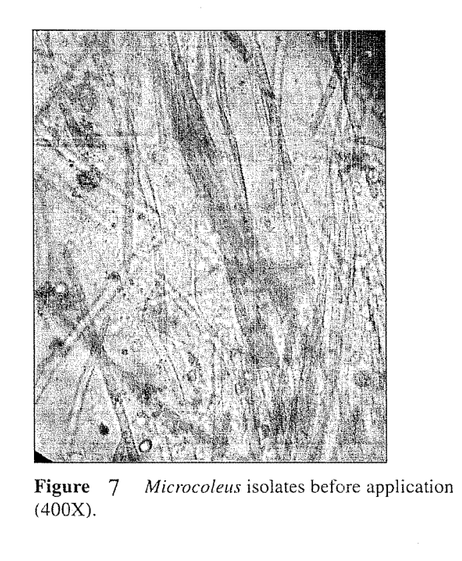

Figure 7 *Microcoleus* isolates before application (400X).

Figures 9A and B

Sterilized soil 17 days after inoculation with 0% (A) and 40% (B) of naturally occurring *Microcoleus*. Strands of *Microcoleus* filaments were visible in the cracks of the soil in the 40% inoculation rate and green colonies were visually apparent on the soil surface. There were no visible filaments in the cracks or colonies on the soil surface on the 0% inoculation.

Figure 10:
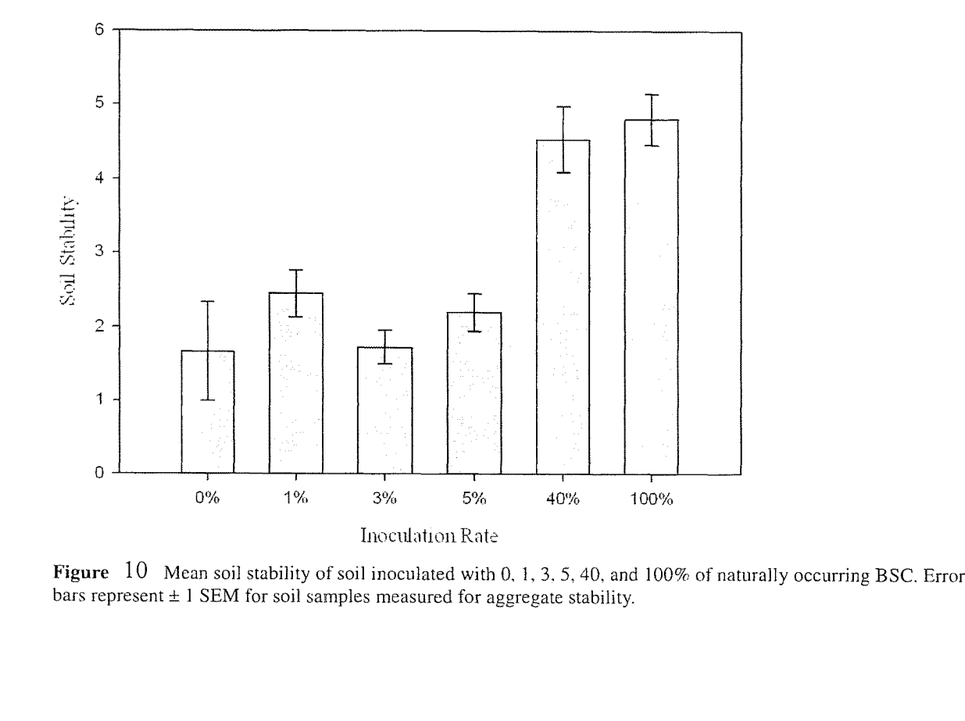

Figure 10 Mean soil stability of soil inoculated with 0, 1, 3, 5, 40, and 100% of naturally occurring BSC. Error bars represent ± 1 SEM for soil samples measured for aggregate stability.

ARID LAND SOIL CRUST RESTORATION

This application claims priority of Provisional Application Ser. No. 61/259,517, filed Nov. 9, 2009, the entire disclosure of which is incorporated herein by this reference.

ACHKNOWLEDGMENT OF NSF SUPPORT AND DISCLAIMER

This material is based upon work supported by the National Science Foundation under Award Number 0810648. Any opinions, findings, and conclusions or recommendations expressed in this publication are those of the author(s) and do not necessarily reflect the views of the National Science Foundation.

BACKGROUND OF THE INVENTION

1. Field of the Invention

The invention relates generally to land restoration and reclamation. More specifically, this invention relates to arid land soil crust restoration by distribution of locally obtained live organisms in a liquid suspension onto the disturbed soil.

2. Related Art

Environmental degradation due to energy exploration, environmental disturbances (e.g. fire), and various land use practices (e.g. grazing) have created conditions in the arid west region of the United States that are increasingly difficult and exceedingly costly to restore with any permanence. To avoid ecosystem collapse and desertification, federal regulatory agencies and private industry are willing and obligated to restore these degraded lands. Despite the critical ecological role of biological soil crusts (BSC) in arid ecosystems, there are few, if any, currently available methods or products for efficiently and affordably inoculating BSC onto disturbed lands.

In the USA West, the need for a sustainable one time application of a product that promotes native diversity while achieving soil stabilization and weed abatement are of immediate concern. Over the course of the next decade, about 100,000 oil and gas wells are slated for construction on public lands across western states, of which about 51,000 will be drilled in Wyoming. Invasion of annual weeds and non-native perennial grasses such as cheatgrass and crested wheatgrass have severely altered western fire regimes. Consequently millions of acres burn each year. Unfortunately, current technology is not well able to effectively and affordably restore these damaged lands.

Between the 2007 fire season that burned 9.2 million acres nationally, not counting wildfires still burning at the end of the year in California, and the expanding energy development across Montana, Wyoming, Colorado, Utah, Nevada, and New Mexico, land in the arid western U.S. land is being destroyed at record rates. Rehabilitation is needed, but without technological advances in restoration practices, the amount of land left environmentally degraded will continue to grow. Biological soil crusts (BSC) are a complex mosaic of cyanobacteria, green algae, lichens, mosses, microfungi, and other bacteria. BSC have a major influence on terrestrial ecosystems, including soil fertility and soil stability; in the arid and semi-arid ecoregions of the world they may constitute as much as 70% of living cover. In the western U.S. BSC are critical components of healthy ecosystems. BSC cover the cold deserts of the Great Basin and Colorado Plateau, the hot deserts of the Mojave and Sonora, and the coastal chaparral shrublands of California. Despite their ecological significance, BSC are not currently part of arid land restoration in any of these areas.

Innovations in restoration are needed to rehabilitate current and future disturbances. Ecological restoration is the attempt to return an ecosystem that has been degraded, damaged, transformed or entirely destroyed as the direct or indirect result of human activities to its natural trajectory. The existing paradigm for rehabilitating land after fires or oil and gas drilling is to replace vegetation through seeding, augment nutrient deficiencies with chemical fertilizers, and control weeds with herbicides. Advancements in seeding equipment designed for wildlands, and the release of native grass germplasms for agricultural production have improved dryland restoration. Still, reestablishing vegetation in the arid desert regions of the West remains challenged by low precipitation and unstable and unfertile topsoil.

U.S. Pat. No. 3,969,844 (Fogel, et al.) discloses a soil treatment method wherein algae in a culture medium containing at least 10% nitrogen are inoculated onto soil, provided with supplemental nutrients and moisture, and allowed to multiply.

*Reclamation and Revegetation Research,* 4 (1986) pp 261-269 is an article entitled "Rapid Stabilization of Fire-Disturbed Sites Using A Soil Crust Slurry: Inoculation Studies", which discloses inoculation of a fine-disturbed site with a soil crust obtained near the burn which had been slurried in water.

*J. Phycol* 29, pp. 140-147 (1993) is an article entitled "Cryptogamic Crusts of Semiarid And Arid Lands of North America", which is a mini-review of the topic of soil algal crusts.

U.S. Published Patent Application No. US 2009/0056214 discloses a method for enhancing soil crust formation by treating disturbed soil with a suspension containing microfloral propagules collected with runoff water from undisturbed sites.

References

Belnap, J. 1994. Potential role of cryptobiotic soil crust in semiarid rangelands. In: Monsen, S. B., and S. G. Kitchen, eds. Proceeding—Ecology and Management of Annual Rangelands. General Technical Report INT-GTR-313. USDA Forest Service, Intermountain Research, Ogden, Utah pp 179-185.

Belnap, J. 2003. Microbes and microfauna associated with biological soil crusts. In: Belnap J. and O. L. Lange, eds. Biological soil crusts: structure, function, and management. Springer, Berlin Heidelberg New York, pp 167-174.

Belnap, J., J. H. Kaltenecker, R. Rosentreter, J. Williams, S. Leonard, and D. Eldridge. 2001. Biological soil crusts: ecology and management. Technical Reference 1730-2. United States Department of the Interior, Bureau of Land Management, Denver, Colo.

Belnap J., R. Prasse, and K. T. Harper. 2003. Influence of biological soil crusts on soil environments and vascular plants. In: Belnap J., and O. L. Lange, eds. Biological soil crusts: structure, function, and management. Springer, Berlin Heidelberg New York, pp 281-300.

Bowker, M. A. 2007. Biological soil crust rehabilitation in theory and practice: an underexploited opportunity. *Restoration Ecology* 15(1): 13-23.

Bowker, M. A., J. Belnap, D. W. Davidson, and H. Goldstein. 2006. Correlates of biological soil crust distribution across a continuum of spatial scales: support for a hierarchical conceptual model. *Journal of Applied Ecology* 43: 152-163.

Bowker, M. A., M. E. Miller, J. Belnap, T. D. Sisk and N. C. Johnson. 2008. Prioritizing conservation effort through the use of biological soil crusts as ecosystem function indicators in an arid region. *Conservation Biology* 22(6):1533-1543.

Boyer, S. L., Johansen, J. R., Fletchner, A. R and Howard, G. L. 2002. Phylogeny and genetic variance in terrestrial *Microcoleus* (Cyanophacea) species based on sequence analysis of the 16S rRNA gene and associated 16S-23S ITS region. *Journal of Phycology* 38(6):1222:1235.

Carlson, R. E. and J. Simpson. 1996. *A Coordinator's Guide to Volunteer Lake Monitoring Methods*. North American Lake Management Society, pp 96.

Hansson, L-A. 1988. Chlorophyll a determination of periphyton on sediments: identification of problems and recommendation of method. *Freshwater Biology* 20:347-352.

Herrick, J. E., W. G.> Whitford, A. G. de Soyza, J. W. Van Zee, K. M. Haystad, C. A. Seybold, M. Walton. 2001. Field soil aggregate stability kit for soil quality and rangeland health evaluations. *Catena* 44:27-35.

Rosentreter, R. and J. Belnap. 2003. Biological Soil Crusts of North America. In: Belnap, J. and O. L. Lange, eds. Biological Soil Crusts: Structure, Function, and Management. Springer. Berlin Heidelberg New York, pp 31-50.

Schwartz, M. W., Hoeksema, J. D., Gehring, C. A., Johnson, N. C., Klironomos, J. N., Abbot, L. K., and Pringle, A. 2006. The promise and the potential consequences of the global transport of mycorrhizal fungal inoculum. *Ecology Letters* 9:501-515.

Snedecor G. W. and W. G. Cochran. 1967. Statistical Methods Sixth Edition. The Iowa State University Press. Ames, Iowa, 593 pp.

ring BSC, wherein the bars represent ±1 SEM for soil samples measured for aggregate stability.

DETAILED DESCRIPTION OF THE INVENTION

Referring to the following detailed description and the figures embedded therein, entitled "Spray-on Biological Soil Crusts for Arid Land Restoration," there are described and shown the preferred, but not the only, embodiments of the invented arid land soil crust restoration methods and compositions.

Spray-on Biological Soil Crusts for Arid Land Restoration

I. Introduction

Biological soil crusts (BSC) are a complex mosaic of cyanobacteria, green algae, lichens, mosses, microfungi, and other bacteria (Belnap et al. 2001). BSC have a major influence on terrestrial ecosystems, including soil fertility and soil stability (Belnap 2003, Belnap et al. 2003); in the arid and semi-arid regions of the world they may constitute as much as 70% of living cover (Belnap 1994). In the western U.S. BSC are critical components of healthy ecosystems. BSC cover the cold deserts of the Great Basin and Colorado Plateau, the hot deserts of the Mojave and Sonora, and the coastal chaparral shrublands of California (Rosentreter and Belnap 2003). The benefits of BSC in the landscape cannot be understated. These benefits include: control of invasive plants through inhibition of germination, soil building, erosion reduction, greater water capture and retention by soils, lessening of severity of dust storms, moderation of fire events through reduction of fine fuels, and greater carbon capture of system due to increased soil stability and fertility.

Despite the ecological importance of BSC's there is currently no method to facilitate establishment of soil crusts on disturbed lands during land restoration or reclamation processes. Three main objectives were identified in exploring the feasibility of restoring native soil crust organisms to disturbed land. The first step in testing feasibility was designing a pressurized spray system for application of BSC in arid land restoration. The spray system would need to keep (BSC) inoculants alive and maintain functionality. The second step of demonstrating feasibility was to re-isolate BSC organisms after they had been sprayed through the tank and determine if the organisms maintained their ability to grow and propagate. The final objective was to show that re-applied BSC protect soil from erosion and nutrient cycling was restored.

This Small Business Innovation Research (SBIR) Phase I research project developed a process for spraying site sourced biological soil crusts (BSC) inoculants onto degraded arid lands in order to facilitate more efficient restoration. The feasibility of spray-on inoculant delivery, ecotype specific BSC organisms isolation, ex situ culture of BSC organisms and restoration potential of inoculants were tested.

II. Methods

Study Area and Collection of Cyanobacteria

BP America is a large producer of natural gas across the Rocky Mountain region and is interested in the potential of spray on biological soils crusts to aid their reclamation efforts (reference letter of support in Phase I proposal). In order to preserve local genetics, minimize the potential risks of changing local ecosystems by the inoculation of non-native organisms (Schwartz et al. 2006), and realize the benefits of local adaptations soils were collected from the Jonah and Moxa Arch natural gas fields in southwest Wyoming. The Jonah field is located in Sublette County and the Moxa field encompasses Lincoln, Sweetwater, Uinta Counties.

The target species for isolation was *Microcoleus vaginatus*, the dominant cyanobacteria in the Great Basin. Cyanobacteria crusts are typically located in the interspaces between perennial shrubs (e.g. *Artemisia* sp., *Atriplex* sp., *Sarcobatus vermiculatus*) and perennial grasses (e.g. *Poa secunda, Elymus Elymoides, Pascopyrum smithii*) in the top 5-10 mm of the soil surface (FIG. 1). During dry conditions cyanobacteria crusts were removed from sedimentary upland soils (FIG. 2). The soil texture was sandy loam (60.7% sand, 29.1% silt, and 10.2% clay).

Isolation and Growth of Cyanobacteria

In the laboratory, collected soil crust fragments (n=20) were measured for surface area. Total cyanobacteria load was then isolated by gently washing the soil crust fragments with deionized water to remove soil from the fibrous filaments followed by repeated soaking and rinsing of the fragments until the majority of soil particles were removed. Careful washing yielded a delicate green mat comprised of tangled filaments. The mat was pressed, blotted dry with paper towels and weighed to obtain a surface area to wet weight ratio. The biomass of naturally occurring hydrated cyanobacteria was 164.73 g/m$^2$.

Once isolated, *Microcoleus* was grown in a 0.5 dilution of Modified Bold 3N media (Table 1) in liquid and on 1.5% agar plates. Cyanobacteria cultures were grown in a temperature controlled room at 25° C. under ambient fluorescent lighting for 12 hr photo periods.

TABLE 1

Modified Bold 3N medium (UTEX 2009)

| # | Component | Amount | Stock Solution Concentration | Final Concentration |
|---|---|---|---|---|
| 1 | NaNO$_3$ (Fisher BP360-500) | 30 mL/L | 10 g/400 mL dH2O | 8.82 mM |
| 2 | CaCl$_2$•2H$_2$O (Fisher 79) | 10 mL/L | 1 g/400 mL dH2O | 0.17 mM |
| 3 | MgSO$_4$•7H$_2$O (Sigma 230391) | 10 mL/L | 3 g/400 mL dH2O | 0.3 mM |
| 4 | K$_2$HPO$_4$ (Sigma P 3786) | 10 mL/L | 3 g/400 mL dH2O | 0.43 mM |
| 5 | KH$_2$PO$_4$ (Sigma P 0662) | 10 mL/L | 7 g/400 mL dH2O | 1.29 mM |
| 6 | NaCl (Fisher A649-500) | 10 mL/L | 1 g/400 mL dH2O | 0.43 mM |
| 7 | P-IV Metal Solution | 6 mL/L | | |
| 8 | Soilwater: GR + Medium | 40 mL/L | | |
| 9 | Vitamin B$_{12}$ | 1 mL/L | | |

Spray System Design

The spray apparatus was designed to expel BSC inoculant from a pressurized tank through a low pressure nozzle (FIG. 3). Ruggedness, portability, and capacity to spray a broad pattern with a large droplet size at low pressures were considered during its design. The spray system could be easily operated and moved by one person. The body for the spray system was made from a 30 gallon air compressor tank. A metal stand was fabricated and welded to the bottom of the tank allowing the tank to be pivoted into an upright position. Charging and spray application were performed with the tank in the upright position; transport and filling of tank with liquid formulations of soil crust organisms is performed with the tank lying horizontal. The pre-existing handle and wheels were maintained in their original position to aid in moving the spray system during use. The liquid fill valve was threaded into the original air fill site on the tank and a 1.5" quick coupler was connected to a 1" male to male 2" pipe fitting to facilitate rapid filling of the tank.

The air inlet placed at the top of the tank connects to the main tank through a low pressure regulator which is connected to a back flow prevention device. An agitation tube mixes the contents of the tank while the tank is pressurized. A pressure gauge located on the low pressure regulator displays the pressure coming from the air compressor to the tank. The main tank pressure gauge shows the pressure in the main tank system. The pressure relief valve serves as a bypass from the main tank line and is used primarily to safely release pressure from the main tank after use and before charging the main tank with liquid.

Figure 4:
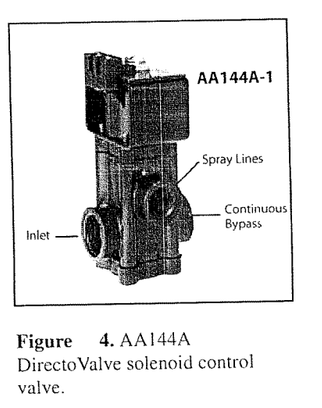

An AA144A Directo Valve™ solenoid control valve (FIG. 4) was threaded directly into bottom of the tank. There is a 90.degree. bend in solenoid casing. The solenoid is actuated by a switch located on the main handle of the spray system. A battery stand was welded below the fill valve to secure the battery to the machine. All three electrical components were wired with a wiring harness run along the tank handle.

The application hose (30') is connected directly to the solenoid. A stainless steel XR TeeJet™ SS8010 nozzle was fitted to the application hose. The low pressure spray capabilities and factory specifications for the XR TeeJet™SS8010 are presented in Table 2.

TABLE 2

Specification for the XR8010 Extended Range Flat Spray Tips (adapted from the TeeJet ™ Catalog 49A, 2004).

|  | PSI | Capacity One Nozzle in GPM[a] | GPA[b] at 4 MPH |
|---|---|---|---|
| TeeJet ™ XR8010 | 10 | 0.41 | 30 |
|  | 15 | 0.61 | 45 |
|  | 20 | 0.71 | 53 |
|  | 30 | 0.87 | 65 |
|  | 40 | 1.00 | 74 |
|  | 50 | 1.12 | 83 |
|  | 60 | 1.22 | 91 |

[a]Gallons per minute
[b]Gallons per acre

Liquid BSC Inoculation of Soils

Bulk soil was homogenized and sieved through a mesh screen prior to sterilization. Soil was sterilized by first dampening it evenly with a spray bottle and then placing it in an oven for two hours at 232° C. Soil was allowed to cool in a laminar flow hood and then approximately 58 g of soil was placed in a petri dish with a surface area of 63.59 cm$^2$. Soil depth in the petri dish was approximately 1 cm.

*Microcoleus* cultures grown in Modified Bold 3N media were sprayed onto the sterilized soil using the pressurized spray system. The liquid inoculant was applied by hand with the nozzle approximately 12 inches above the soil surface (FIG. 5). *Microcoleus* was applied at six different rates, 0 (control), 1, 3, 5, 40, and 100% of naturally occurring cyanobacteria levels.

Measure of Total Chlorophyll in Inoculated Soils

Seventeen days after inoculation total chlorophyll was extracted from the soil samples with 25.0 ml of 100% acetone (Hansson 1988). The extraction took place in the dark for 15 hours at 5° C. Samples were shaken twice during the extraction period. Samples were filtered (VWR 474 filter paper), and absorbance of the extracts was measured at 665 and 750 nm in 1 cm glass cuvettes (3 ml) on a Thermo Genesys 20 spectrophotometer. Spectrophotometer readings were converted to total chlorophyll utilizing the following formula from Carlson and Simpson (1996):

$$\text{Total Chlorophyll}=11.0(Abs_{665}-Abs_{750})\ (v/Vp)$$

The total chlorophyll formula was used to determine total μg of chlorophyll per soil surface area. Absorption at 750 nm provides a measure of turbidity which is subtracted from the 665 nm absorption data which provides a measure of photosynthetic pigments. The volume of acetone utilized for the extraction is represented by v and p is the pathlength of the spectrophotometer. The absorption coefficient used for acetone was 11.0.

Soil Aggregate Stability

Soil surface stability was measured using an aggregate stability test (Herrick et al. 2001). A soil ped approximately 6-8 mm was submerged in 2.5 cm of deionized water for five minutes on a 1.5 mm mesh screen. Soil peds were given a rank score between 1 (50% of structural integrity lost within 5 seconds of insertion in water) and 6 (>75% of soil remained on sieve after 5 minutes and five dipping cycles) based on soil structure integrity after wet sieving. Soil stability was measured in triplicate from samples in each treatment group.

Statistics

Data were analyzed using the Mann-Whitney rank sum test (Snedecor and Cochran 1967). All statistics were performed at $\alpha=0.05$.

III. Results

Cyanobacteria Isolation and Application

Cyanobacteria filaments identified as *Microcoleus* sp. by their morphology were successfully isolated from soils collected from the Jonah and Moxa oil and natural gas fields (FIG. 6). The phylogeny of *Microcoleus* is currently under revision and cyanobacteria were identified to genus (Boyer et al. 2002).

Spray System Performance

*Microcoleus* sprayed through the pressurized spray system at 10 psi retained cell structure (compare FIGS. 7 and 8). *Microcoleus* sprayed onto 1.5% agar plates made with Modified Bolds 3N media showed active growth for 17 days following application.

BSC Inoculation of Soil

*Microcoleus* survived liquid sprayed application onto sterilized soil at all spray concentrations (1, 3, 5, 40, and 100% of naturally occurring levels) 17 days post application. FIGS. 9A and B show soil sprayed with 0 and 40% of naturally occurring levels of cyanobacteria 17 days after inoculation. The extent of colonization on the disturbed soil by *Microcoleus* was readily apparent by visual inspection.

The total chlorophyll analysis results varied within and across inoculation treatment groups (Table 3). Chlorophyll was detected in each treatment group 17 days post application. Sample size was not held constant between treatment groups due to soil plates not meeting homogeneity standards. The maximum total chlorophyll value was higher in the soil samples treated with 40% and 100% of naturally occurring BSC than soil inoculated with lower concentrations. Despite measured contamination of the control group there was a significant difference ($P<0.05$) between the total chlorophyll content in 1% of naturally occurring cyanobacteria treatment compared to the 0% control group (Table 3).

TABLE 3

Total chlorophyll extracted 17 days after inoculation with 0, 1, 3, 5, 40, and 100% of naturally occurring Microcoleus on soil. Minimum, maximum, mean and standard deviation (SD) is given for total chlorophyll for soil samples based on inoculation rate.

| Treatment | Sample size (n) | Total Chlorophyll (mg/m$^2$) | | |
|---|---|---|---|---|
| | | Min-Max | Mean | SD |
| 0% | 3 | 0-1.47 | 0.95 | 0.82 |
| 1% | 7 | 1.99-3.97 | 2.94 | 0.74 |
| 3% | 9 | 1.30-2.59 | 1.99 | 2.43 |
| 5% | 8 | 1.30-4.32 | 2.38 | 0.96 |
| 40% | 6 | 0.78-8.73 | 3.52 | 2.74 |
| 100% | 1 | 7.96 | n/a | n/a |

BSC Effects on Soil Stability

The application of liquid BSC through the designed spray system increased soil aggregate stability compared to the control group (FIG. 10). The mean soil stability of soils inoculated with 1 and 5% of naturally occurring cyanobacteria was higher than the control, but the differences were not significant. Soil stability of the control group varied considerably affirming the contamination detected in the chlorophyll extraction. There was a significant difference in soil stability between soils inoculated with 0, 1, 3, and 5% naturally occurring cyanobacteria and soils in the 40 or 100% treatment groups (P<0.05). Soils displaying high aggregate stability had an identifiable mat of soil crust holding soil particles together upon completion of the five wet sieve dipping cycles.

IV. Discussion

The results of this SBIR Phase I research project for developing a process for spraying site sourced biological soil crusts (BSC) inoculants onto degraded and land show that site-specific cyanobacteria can be isolated and cultured to obtain enough material for research scale applications. The results also show that isolated *Microcoleus* cultures survived application through a pressurized spray delivery system at 10 psi. In sum, these results constitute the first technical objective stated in the SBIR Phase I proposal. Colonization of soils by spray-on BSC demonstrates the second technical objective except that survivability of the technology in extreme growth environments was not evaluated.

The third technical objective, to prove that ecosystem function was improved with an application of BSC and liquid soil formulations was not demonstrated. However, the BSC contribution to the ecological function of arid environments is well documented (Belnap et al. 2001, Belnap et al. 2003, Bowker et al. 2008).

Soils inoculated with liquid BSC inoculants exhibited increased soil stability which demonstrated the fourth and final objective of the feasibility study. Two noteworthy corollaries to these results were that colonization was detected at inoculation rates of 1% of naturally occurring levels of cyanobacteria, and enhanced soil surface stability was observed within 17 days of inoculation. These results suggest that the technology merits scaling up to treat sizeable disturbances, and that the desired effects of BSCs may be recognized in a relatively short timeframe post spray-on application.

Problems Encountered and Methods of Resolution Used

Several problems were encountered during the Phase I research process. Some of the challenges led to new innovations while others diluted the statistical strength of the Phase I findings. The problems do not indicate that the feasibility of spraying ex situ cultures of BSC onto disturbed ground will not work, only that experimental execution and mechanical challenges need to be refined when moving forward with scale-up and field testing.

Taking the filamentous morphology of *Microcoleus* into consideration led to the conclusion that the spray delivery system needed to be redesigned from the initial proposed spray system for Phase I project. The original spray system used a centrifugal pump to move fluids from a large holding tank to the nozzle. Potential damage from the shearing force of the pump's impellors and the internal pressures of the pump, 45-50 psi, were estimated to be potentially very damaging to *Microcoleus*. Alternative pumps, such as a piston pump, operate with high internal pressures and have small ports which were determined to be unsuitable. Taking this into account, the delivery system was redesigned and a pressurized tank system was built as described in the methods section.

Maintaining a homogeneous suspension of *Microcoleus* solution in the tank was another challenge associated with the spray system. To resolve this issue the air fill tube was elongated to reach the bottom of the tank when it is in the vertical spray position. The compressed air used to charge the tank also served to agitate the inoculant solution which was intended to create a more even suspension. In practice, the spray system performed well. *Microcoleus* survived the delivery and inoculant was detectable at all spray rates. However, the results showed that there was negligible difference between chlorophyll content and soil aggregate stability between the 1, 3, and 5% treatment groups indicating that the spray system is not capable of resolving differences at low concentrations. Planned improvements for the spray system include the addition of a pressure regulator to provide constant agitation as inoculant is being applied, coating the inside of the tank with Teflon, and designing a mechanical scraper inside the tank to keep cyanobacteria from splashing and sticking to the tank walls.

A mechanical set back encountered during the Phase I research period was the break down of the cooling and humidity control systems on the Conviron S1H0 growth chamber. The chamber was going to be used to incubate soils inoculated with liquid slurry of *Microcoleus* under approximate environmental conditions of the Great Basin. Extreme environmental conditions such as very warm summer and very cold winter temperatures, intense solar radiation (UV), infrequent precipitation and low humidity are potential factors that can limit cyanobacteria growth and survivorship. Without the chamber, a climate controlled lab was used for incubating soil test plates after inoculation. While the survivorship and growth of inoculated soils is promising to scale up and field test the spray on crust technology, the growth conditions were not as extreme as described in the Phase I project description. Determination of extreme survival conditions under laboratory conditions will serve to inform physical operational restrictions. The common sense approach based on regional ecology indicate, that climactic conditions in the late fall and early spring will allow for survival of spray-on BSC technologies. As the technology is expanded, and especially as multiple species are incorporated in the inoculums, knowledge of acceptable post-application environmental parameters will be critical.

Laboratory execution problems during the Phase I research included contamination of the 0% control treatments of cyanobacteria inoculum and difficulty producing a homogeneous soil surface inside the petri dish for testing. The soil sterilization technique used left residual BSC in the soil. The contaminated controls were not detected until total chlorophyll was measured. The contamination affected the growth and stability tests and impacted the ability to measure differences between controls and the lower application rates. Small sample sizes also hampered the ability to detect differences among treatments. Even so, the results still show that there are some significant contributions to cyanobacteria colonization and soil stability as a result of liquid spray-on BSC inoculants. All the results indicate a positive correlation between inoculation rate and cyanobacteria colonization and soil stability.

The irregularity in soil surface texture and soil moisture resulted in uneven sample sizes among treatment groups. Plate preparation for future testing will employ a finer soil sieve to homogenize the soil and exclude rock aggregates. The irregular soil surface texture confounded the outcome of the lab portion of this stage of technology development, but is not expected to pose difficulties during field application. In the field, surface roughness and microtopography is actually beneficial as it creates microhabitats for BSC (Bowker et al. 2006).

Problems Remaining or Unfilled Research Objectives

Together with *Microcoleus* the early colonizing moss, *Pterygoneurum*, was planned for testing as an additive in the spray-on inoculant formulation. It was hypothesized that utilizing multiple BSC species in inoculations would augment the natural biodiversity of the ecosystem and increases the probability of recovery by enabling microsite selection. Efforts to expand moss cultures were aborted after three weeks of trials because of slow reproduction and culture contamination. Attempts to expand moss cultures are ongoing. While the current formulation of the inoculum does not have as many BSC species as originally proposed, culture and application of the primary target, *Microcoleus*, was achieved.

Soil microbe formulations consisting of compost tea extracts were going to be tested as a component of the BSC liquid formulation. The effects of soil microbe formulations on BSC survivability, and potential synergistic benefits toward improved soil nutrient cycling were not included in the Phase I study due to lack of time and limited availability of BSC cultures for materials to increase sample size.

V. Conclusion

This (SBIR) Phase I study developed a process for spraying site sourced biological soil crusts (BSC) inoculants onto degraded and lands in order to facilitate more efficient restoration. The results show that the proposed innovation of delivering liquid cultures of *Microcoleus* onto soil facilitates assisted recovery of the native cyanobacteria community and imparts stability to the soil surface. The precision of the spray system at resolving differences of low application rates at the scale of a petri dish was indeterminate. Controlled tests of how spray-on soil crusts contribute to soil nutrient cycling or improvement of seedling growth remain unfilled. These problems notwithstanding the data from this initial research demonstrate that low rates of BSC application survive and grow on soils with no extra additives. In addition, the trademark ecological benefit of BSC, soil surface stability, was increased after only 17 days of growth. Given that BSC are slow to recolonize an area post disturbance (Bowker 2007) these findings warrant further research into field applied liquid BSC inoculant on oil and natural gas fields and on wildfire burn areas.

Although this invention has been described above with reference to particular means, materials and embodiments, it is to be understood that the invention is not limited to these disclosed particulars, but extends instead to all equivalents within the broad scope of the following claims.

The invention claimed is:

1. A process for restoring disturbed arid land soil crusts, comprising:
   obtaining soil crust from near the disturbed site;
   culturing *Microcoleus* from the obtained soil crust;
   distributing the live cultured *Microcoleus* in a liquid suspension to form an inoculant; and,
   distributing the inoculant onto the disturbed site in a live form and in an amount that provides about 1% to about 100% of the indigenous *Microcoleus* population at the disturbed site before the need for restoration began.

2. The process of claim 1 wherein the inoculant *Microcoleus* community is similar to the type of the one existing at the disturbed site before the need for restoration began.

3. The process of claim 1 wherein the *Microcoleus* are extracted from the soil crust with water prior to culturing.

4. The process of claim 3, wherein the cultured *Microcoleus* are distributed in a water suspension.

5. The process of claim 1 wherein fertilizer, nutrients, preservatives and/or conditioners are added to the suspension.

6. The process of claim 1 wherein the *Microcoleus* is distributed in an amount that provides about 1% to about 40% of the indigenous population at the disturbed site before the need for restoration began.

7. The process of claim 6 wherein the *Microcoleus* is distributed in an amount that provides about 2% to about 5% of said indigenous population at the disturbed site before the need for restoration began.

8. The process of claim 6 wherein the *Microcoleus* is distributed in an amount that provides about 1% to about 3% of said indigenous population at the disturbed site before the need for restoration began.

9. The process of claim 6 wherein the amount of *Microcoleus* is distributed in an amount that provides about 3% to about 5% of said indigenous population at the disturbed site before the need for restoration began.

10. The process of claim 1 wherein the *Microcoleus* is distributed in an amount that provides about 40% to about 100% of said indigenous population at the disturbed site before the need for restoration began.

11. The process of claim 1 wherein the inoculant is distributed onto the disturbed site with a pressurized spray system at up to about 10 pounds per square inch (psi).

12. The process of claim 11 wherein the *Microcoleus* retain cell structure.

* * * * *